(12) United States Patent
Cosson et al.

(10) Patent No.: US 8,986,190 B2
(45) Date of Patent: Mar. 24, 2015

(54) IMPLANT FOR TREATING A GENITAL PROLAPSE, AND ASSOCIATED TREATMENT METHOD

(75) Inventors: Michel Cosson, Lambersart (FR); Philippe Debodinance, Coudekerque Branche (FR); Bernard Jacquetin, Clermont-Ferrand (FR)

(73) Assignees: Centre Hospitalier Regional Universitaire de Lille, Lille (FR); Universite de Droit et de la Sante de Lille 2, Lille (FR)

( * ) Notice: Subject to any disclaimer, the term of this patent is extended or adjusted under 35 U.S.C. 154(b) by 135 days.

(21) Appl. No.: 13/131,857

(22) PCT Filed: Nov. 27, 2009

(86) PCT No.: PCT/EP2009/065965
§ 371 (c)(1),
(2), (4) Date: Sep. 12, 2011

(87) PCT Pub. No.: WO2010/060984
PCT Pub. Date: Jun. 3, 2010

(65) Prior Publication Data
US 2012/0016186 A1 Jan. 19, 2012

(30) Foreign Application Priority Data
Nov. 28, 2008 (FR) ...................................... 08 58139

(51) Int. Cl.
*A61F 2/00* (2006.01)

(52) U.S. Cl.
CPC .................................... *A61F 2/0045* (2013.01)
USPC ............................................................ 600/37

(58) Field of Classification Search
USPC .................................. 600/29–30, 37; 606/151
See application file for complete search history.

(56) References Cited

U.S. PATENT DOCUMENTS

| 5,824,082 A | * | 10/1998 | Brown ....................... 623/11.11 |
| 6,595,911 B2 | * | 7/2003 | LoVuolo .......................... 600/30 |
| 6,610,006 B1 | * | 8/2003 | Amid et al. ...................... 600/37 |
| 6,669,735 B1 | * | 12/2003 | Pelissier .................... 623/23.74 |
| 2007/0049790 A1 | * | 3/2007 | Wagner et al. .................. 600/37 |
| 2008/0161837 A1 | | 7/2008 | Toso et al. |
| 2009/0082792 A1 | * | 3/2009 | Koyfman et al. ............. 606/151 |
| 2010/0261950 A1 | * | 10/2010 | Lund et al. ...................... 600/30 |

FOREIGN PATENT DOCUMENTS

WO    WO 2006/069078 A2    6/2006

* cited by examiner

*Primary Examiner* — Samuel Gilbert
(74) *Attorney, Agent, or Firm* — Blakely Sokoloff Taylor & Zafman

(57) ABSTRACT

The invention relates to an implant (1) or prosthesis for treating a genital prolapse, characterized in that it comprises a support portion (41, 51), which has been preformed with a hollow shape in order to match the shape of an organ that is to be supported, and one or more bearing portions (42, 52), which extend away from the support portion (41, 51) so as to bear on bone or ligament structures in order to stabilize the implant.

12 Claims, 8 Drawing Sheets

IMPLANT FOR TREATING A GENITAL PROLAPSE, AND ASSOCIATED TREATMENT METHOD

This is a non-provisional application claiming the benefit of International application number PCT/EP2009/065965 filed Nov. 27, 2009.

FIELD OF THE INVENTION

The invention concerns an implant or prosthesis for treating pelvic organ prolapse.

STATE OF THE ART

Pelvic organ prolapse is a descending of pelvic organs (bladder and/or uterus and/or rectum) from their normal position when they tend to protrude through the vulvo-vaginal opening. This phenomenon results from weakening of the supportive, cohesive and organ-suspending systems. The three visceral compartments of the pelvis may be concerned: anterior compartment (urinary), middle compartment (genital) and posterior compartment (digestive).

The maintaining of normal pelvic-perineal anatomy is based on the three systems having synergic action: a suspending system (ligaments), cohesive system (connective tissue between the different organs) and supporting system (levator ani muscle joining between the vulva and the anus to form the perineal central fibrous core). Normally, the resultant of intra-abdominal pressure forces is oriented towards the posterior perineum and sacral cavity, preserving the weak point formed by the uro-genital slit. When pelvic statics are perturbed, the resultant of the pressure forces places demand on the uro-genital slit.

The aetiology of prolapses is multi-factorial, schematically with two elements causing disruption of pelvic static balance: degradation of the anatomical structures and excessive pressure load imposed thereupon. The essential factor is obstetrical trauma: childbirth is responsible for pelvic-perineal lesions of greater or lesser extent. Amongst the other factors mention may be made of congenital predisposition (ligament laxity, connective tissue anomalies), ageing, menopausal hormone deficiency and obesity.

The symptoms associated with prolapse are variable and may in particular include feelings of pelvic heaviness, pelvic-lumbar pain, obstructive urinary syndromes with or without urinary or faecal incontinence. The seriousness of pelvic organ prolapse is especially evaluated in relation to its impact on patients' quality of life in terms of functional discomfort.

Pelvic organ prolapse is a frequent pathology whose prevalence is estimated at between 30 and 50% of women irrespective of the type of prolapse and/or the stage thereof.

A distinction can be made between several types of prolapse:

Uterine prolapse is characterized by the disappearance of structures supporting the uterus. As a result this organ slips down into the vagina.

Prolapse of the vaginal vault is often observed after a hysterectomy. The top portion of the vagina may be pushed through the vagina towards the outside.

Enterocele occurs with prolapse of the top of the vagina, sometimes after hysterectomy. Pouch of Douglas hernia may occur, occupied by the intestine or omentum.

Cystocele (also called prolapse of the anterior wall of the vagina) occurs when the anterior wall loses its supporting structures. The bladder descends into the vagina.

Rectocele (also called prolapse of the posterior wall of the vagina) occurs when the posterior wall loses its supporting structures leading to descending of the rectum into the vagina.

Depending upon the stage or seriousness of prolapse, different treatments are offered to the patient. A distinction is made between non-surgical and surgical treatments.

Non-surgical treatments comprise perineal rehabilitation to strengthen the levator ani muscles in order to improve pelvic statics.

In addition, there are numerous surgical techniques for treating prolapse consisting of inserting implants or prostheses to give support to the prolapsed organ.

Documents WO2004/091443 A2, WO2007/081954 A1 and FR2871365 A1 describe implants comprising a body of general rectangular shape with suspending arms in the form of harnesses extending from the body. The suspending arms are used to attach the body to the utero-sacral ligaments.

However, the placing in position of these implants requires heavy surgery, comprising anaesthesia of the patient, a dissection phase and a positioning phase using perforating guides. These instruments may lead to injury of the blood vessels and nerves, or carry a risk of organ perforation. The implants are attached by means of the arms using sutures. The stability of these implants depends upon the strength of the suture made in the ligaments.

Document WO2004/091443 A2 specifies that the holding in place of the implant is mainly ensured by friction between the implant and the tissues through which it passes.

Additionally, these implants do not allow satisfactory supporting of the organs. In particular, it is frequently observed that these implants have a tendency to retract.

Also, these implants do not have optimum spatial stability and ill adapt to the patient's anatomy.

Finally, the attachment of these implants by suspension arms can lead to pain in particular at the emerging point of these arms.

It follows that these implants do not always allow good return to the physiological situation of the pelvic organs.

Document WO2005/046511 A2 describes a pelvic implant intended to be placed in the pelvic cavity without any sutures. The implant comprises a flexible sheet including a first and a second layer, and a frame positioned between the two layers. The frame comprises two pivot arms. The placing in position of this implant requires incision of the vaginal wall. By actuating the pivot arms, the implant can be brought into a folded configuration in which the implant can be inserted through the vagina and arranged between the vagina and the bladder. The implant is then brought to a deployed configuration in which the arms come to support themselves against the side walls of the pelvis.

Although positioning of this implant is facilitated and requires less heavy surgery than needed for positioning the implant described in document WO2004/091443 A2, the implant in document WO2005/2005/046511 A2 has several disadvantages.

In particular, this implant is not adapted to the different types of anterior or posterior prolapse.

In addition, this implant cannot accommodate dynamic pressures existing in the abdomen. In the event of sudden exertion by the patient, it is highly likely that the implant will not remain in its initial position but on the contrary will move within the cavity.

The shape of this implant does not allow it to bear upon adjacent bone or ligament anatomical structures.

Finally, the frame is located at the urethra, which may give rise to problems and to pain on voiding.

PRESENTATION OF THE INVENTION

It is one objective of the invention to propose an implant for treating a pelvic organ prolapse, which can be held in position during the healing period.

This problem is solved with the present invention by means of an implant for treating pelvic organ prolapse, characterized in that it comprises a preformed hollow-shaped supporting portion for mating the shape of the organ to be supported, and one or more bearing portions extending from the supporting portion that come to bear upon bone or ligament structures in order to stabilize the implant.

The expression "preformed" in the context of the present invention means that the supporting portion is not planar but naturally has a three-dimensional shape.

The preformed supporting portion allows good adaptation of the implant to the anatomy of the organ to be supported. Since the supporting portion mates the shape of the organ, the implant tends to self-position itself correctly relative to the organ. This allows facilitated positioning of the implant and improves the stability thereof under conditions of daily movements.

In addition, the preformed supporting portion allows re-positioning of the prolapsed organ and adjacent organs in more physiological and anatomical manner than with existing implants.

The bearing portions contribute towards correct self-positioning of the implant.

Since the implant does not comprise any suspending arms, the implant does not require the use of perforating guides, and thereby avoids the onset of pain at points of emergence.

The implant may have the following characteristics:
- the supporting portion has a contour of general oval or elliptical shape,
- the implant comprises a soft membrane and a bracing to hold the membrane taut,
- the soft membrane comprises a web comprised of interlaced fibres,
- the soft membrane comprises polypropylene, polyester or a material of animal or human origin,
- the bracing is able to be folded allowing insertion of the implant in the tissues as far as a working position, and able to be deployed when the implant reaches the working position,
- the bracing is able to deploy itself spontaneously,
- the bracing is formed of an absorbable material,
- the implant comprises a first hollow-preformed supporting portion to support the bladder, and a second hollow-preformed supporting portion to support the rectum,
- the implant comprises a connecting part between the first supporting portion and the second supporting portion,
- the connecting part comprises a zone of lesser resistance which can be broken to separate the first supporting portion from the second supporting portion.

The invention also relates to a method for treating pelvic organ prolapse, comprising a step of:
- making an incision in a wall of the vagina to form a space between the vagina and an organ to be supported,
- arranging in the space an implant such as previously defined, in a position in which the hollow-preformed supporting portion mates the shape of the organ to be supported and the bearing portion(s) come to bear upon bone or ligament structures to stabilize the implant.

PRESENTATION OF THE FIGURES

Other characteristics and advantages will become further apparent from the following description which is solely illustrative and non-limiting, and is to be read with reference to the appended figures among which.

DETAILED DESCRIPTION OF ONE EMBODIMENT

Figure 1:
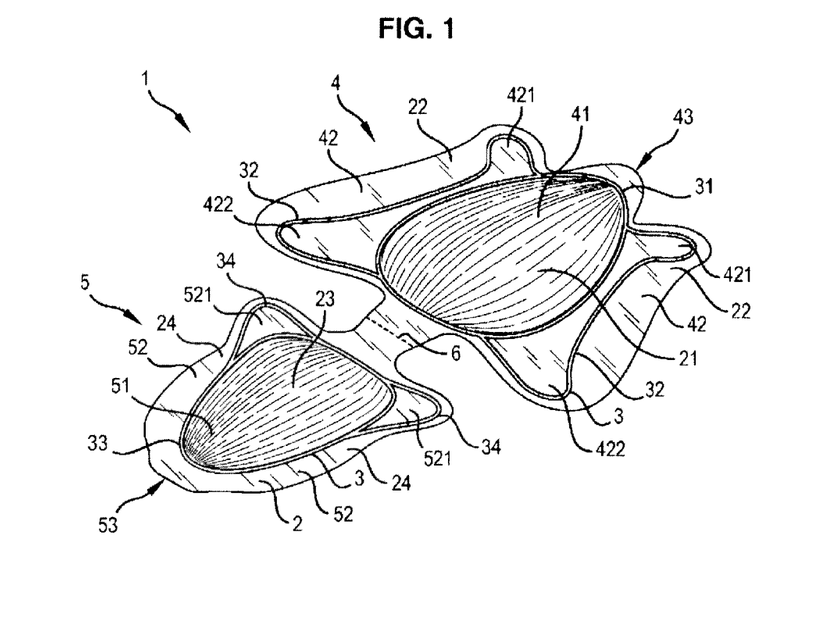
FIG. 1 is a schematic perspective view of an implant for treating pelvic organ prolapse conforming to one embodiment of the invention.
Figure 2:
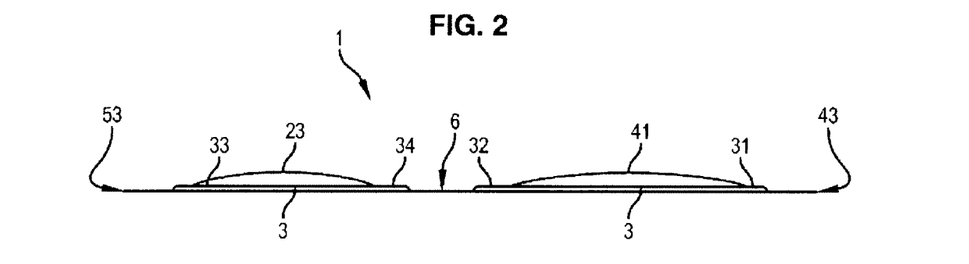
FIG. 2 is schematic profile view of the implant in FIG. 1, FIGS. 3A-3B to 9A-9B schematically illustrate variants of implants conforming to one embodiment of the invention.

In FIGS. 1 and 2 the implant 1 shown is comprised of a soft membrane 2 and a bracing assembly 3.

The implant illustrated FIG. 1 is a total implant: it comprises a first part 4 (anterior part) intended to support the bladder and a second part 5 (posterior part) intended to support the anus, as well as a connecting part 6 (intermediate part) between the first part 4 and the second part 5. The connecting part 6 can easily be sectioned so that the first part 4 can be separated from the second part 5 if needed. For this purpose, the connecting part 6 may comprise a zone of lesser resistance which can easily be broken to separate the first part from the second part.

The first part 4 is of general trapezoid shape. This part 4 comprises a first central supporting portion 41 intended to mate the shape of the bladder, and lateral bearing portions 42 (comprising two proximal bearing portions 421 and two distal bearing portions 422) extending from the supporting portion 41 which come to bear upon bone or ligament structures located in the vicinity of the bladder to stabilize the implant.

The supporting portion 41 comprises a portion 21 of the soft hollow-preformed membrane. In other words, the soft membrane 2 is not planar but naturally has a three-dimensional shape at the supporting portion adapted to fit around the shape of the bladder.

The supporting portion 41 also has a contour of general oval or elliptical shape.

The supporting portion 41 comprises bracing 31 of general oval or elliptical shape extending along the contour and defining a frame on which the portion 21 of the membrane is fixed.

The bearing portions 42 comprise planar portions 22 of the soft membrane, and bracing 32 to hold the planar portions taut. The bearing portions 42 form wings adapted to stabilize the implant when it is positioned in the patient's body to support the bladder.

The second part 5 is of general triangular shape. This part 5 comprises a first central supporting portion 51 intended to mate the shape of the rectum, and lateral bearing portions 52 (comprising two proximal bearing portions 521) extending from the supporting portion 51 which come to bear upon bone or ligament structures located in the vicinity of the rectum to stabilize the implant.

The supporting portion 51 comprises a portion 23 of the hollow-preformed soft membrane. In other words the soft membrane 2 is not planar but naturally has a three-dimensional shape at the supporting portion adapted to fit around the shape of the rectum.

The supporting portion 51 also has a contour of general oval or elliptical shape.

The supporting portion 51 comprises bracing 33 of general oval or elliptical shape extending along the contour and defining a frame on which the membrane portion 23 is fixed.

The lateral bearing portions 52 comprise planar portions 24 of the soft membrane and bracing 34 allowing the planar portions to be held taut. The lateral bearing portions 52 form wings adapted to stabilize the implant when it is positioned in the patient's body to support the anus.

The hollow-preformed supporting portions 41 and 51 allow physiological re-positioning of the bladder ahead of the uterus and rear-lying rectum. The portions 41 and 51 are adapted to the patient's normal anatomy. The dimensions of these portions may vary: they generally have a length and width of the order of several centimeters and a depth of the order of 1 centimeter. The dimensions can be adapted to the specific anatomy of a patient or group of patients.

The soft membrane can be formed of a biocompatible web or synthetic fabric having a basic weft in non-absorbable material such as polypropylene, polyester or a material of animal of human origin.

The three-dimensional shape of the membrane 2 (in particular the hollow-shaped portions 21 and 23) can be obtained by moulding the membrane or by deformation thereof by applying a solid form under heat. The three-dimensional shape can also be obtained via knit or weave of the membrane, i.e. by specific interlacing of the fibres forming the web or fabric so that the membrane naturally forms a hollow. Preforming of the membrane allows hollow-shaped supporting portions 41 and 51 to be obtained that are adapted to mate the shape of the organs to be supported.

The bracings 31, 32 and 34 allow the implant to be held in place temporarily within the dissection spaces during the healing phase.

The bracing assembly 3 including the bracings 31, 32, 33 and 34 is formed of an absorbable material. By "absorbable" under the present invention is meant the characteristic according to which the material of the bracings is absorbed by the biological tissues and disappears in vivo after a given period. The material can be chosen so that this period corresponds to the time needed for healing. This period is substantially less than 4 months for example.

The material forming the bracing assembly 3 is sufficiently elastic so that the implant is able to be folded by merely exerting pressure between the fingers without the implant breaking or being definitively deformed, and so that the implant is spontaneously deployed when the pressure exerted on the implant is released. More precisely, the bracing assembly is adapted to be folded to allow insertion of the implant in the dissection spaces of the tissues as far as a working position, and to be deployed when the implant is in the working position.

Therefore the membrane 2 is held taut by the bracing assembly 3 during the healing phase, which reduces the risk of secondary retraction of the implant thereby reducing the risk of recurrence.

The implant 1 comprises at least one cut-out (not illustrated) formed in one of the corners of the first trapezoid-shaped part 4 or of the second triangular-shaped part 5. The cut-out is able to receive a finger or instrument to push at least one end of the implant 1 with the finger or blunt instrument for correct positioning of the implant. In one preferred embodiment of the invention, the implant comprises four cut-outs located at the four corners of the first trapezoid-shaped part 4.

When positioning the implant 1, the anterior end 43 is intended to be located underneath the bladder whilst the posterior end 53 is free at the fork point.

The implant can be inserted with the fingers or using a blunt instrument for positioning thereof, and can be associated with a reinforcement system e.g. glue or temporary intra-vaginal device.

Different models and variations of implants can be developed to meet specific groups of patients or patients having specific needs: preserving the uterus, hysterectomy, recurrence, small-size or voluminous prolapse, anatomical variants. The shape of the prosthesis is not limiting and can be defined in relation to the patient's anatomy and specifically conformed subsequent to prior clinical examination or preoperative imaging. The same applies to the rigidity of the implant. Smaller or larger sizes, more or less oval, round, square, moderately or more than moderately convex can be designed along the same general principle.

The implant is preferably put in place via vaginal route, but positioning via coelioscopy or laparotomy can also be envisaged. The shape and size of the implant can then be adapted to the positioning mode. The implant can also be used for treating stress urinary incontinence, or inguinal or femoral hernias or even wall inversion.

FIGS. 3A-3B to 9A-9B schematically illustrate variants of implants conforming to one embodiment of the invention.

Figure 3A:
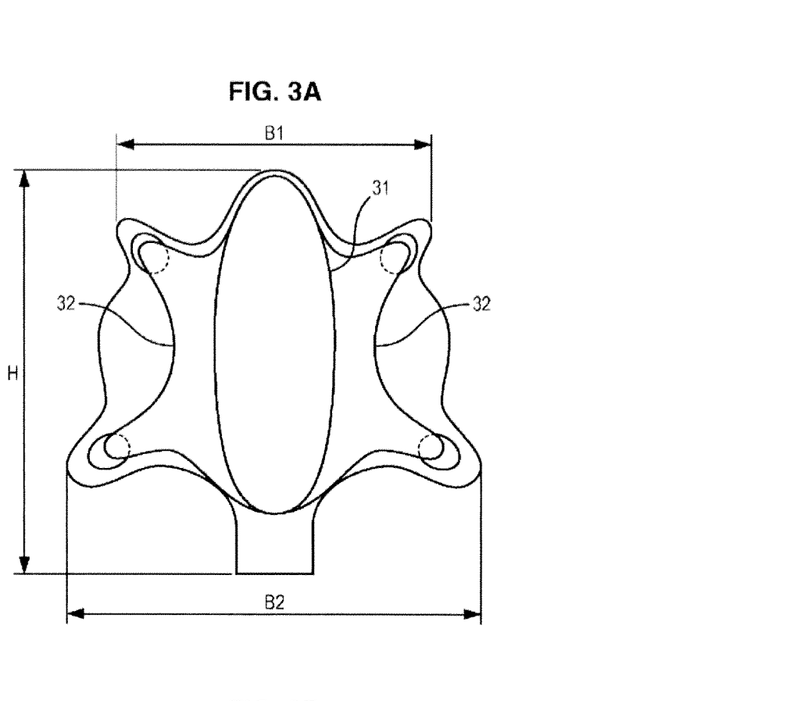
Figure 3B:
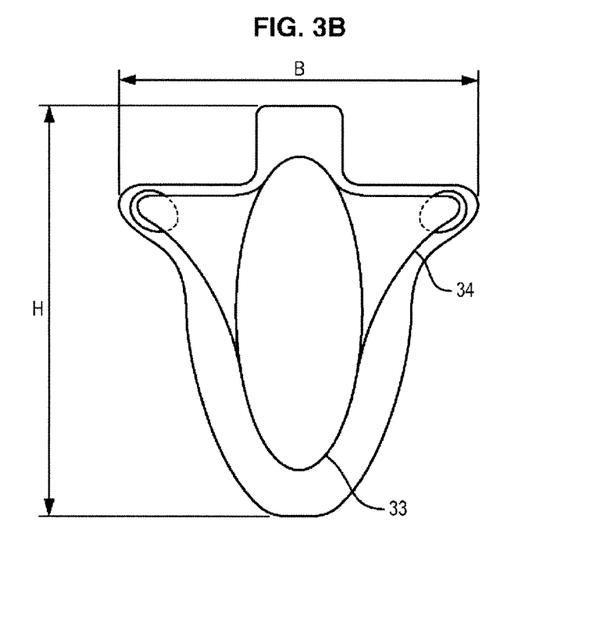

According to a first variant shown FIGS. 3A and 3B, the implant comprises an anterior part (FIG. 3A) of trapezoid shape. The anterior part has a short side (B1) of length ranging from 7 to 11 centimeters (preferably 11 centimeters), a long side (B) of length ranging from 10 to 14 centimeters (preferably 12 centimeters), and a height (H) ranging from 10 to 14 centimeters (preferably 12 centimeters). The long side (B2) of the trapezoid corresponds to the posterior part of the implant.

The posterior part (FIG. 3B) is in the shape of an isosceles triangle. The posterior part has a base (B) with a length of between 7 and 11 centimeters (preferably 9.5 centimeters) and a height (H) of between 9 and 13 centimeters (preferably 11 centimeters). The base (B) of the triangle forms the anterior part of the posterior part. The posterior implant has at least one cut-out located at the base of the triangle. In one preferred embodiment, the implant comprises two cut-outs located at the base of the triangle.

Figure 4A:
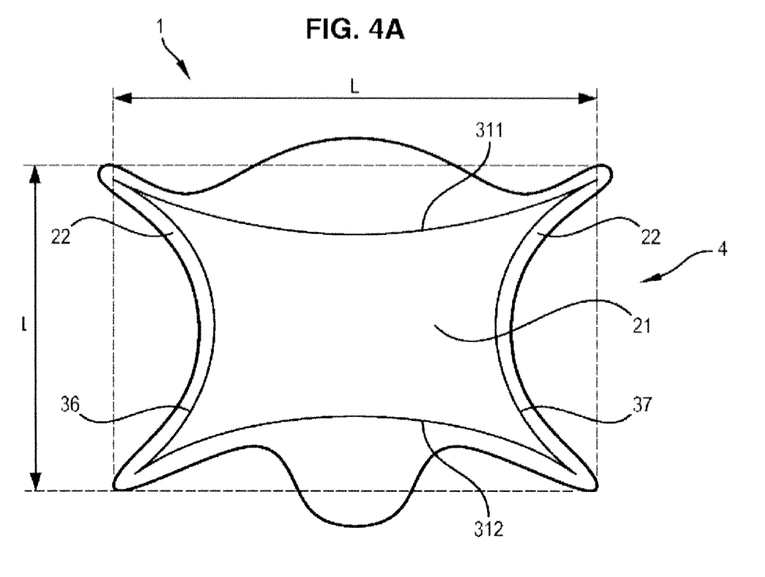
Figure 4B:
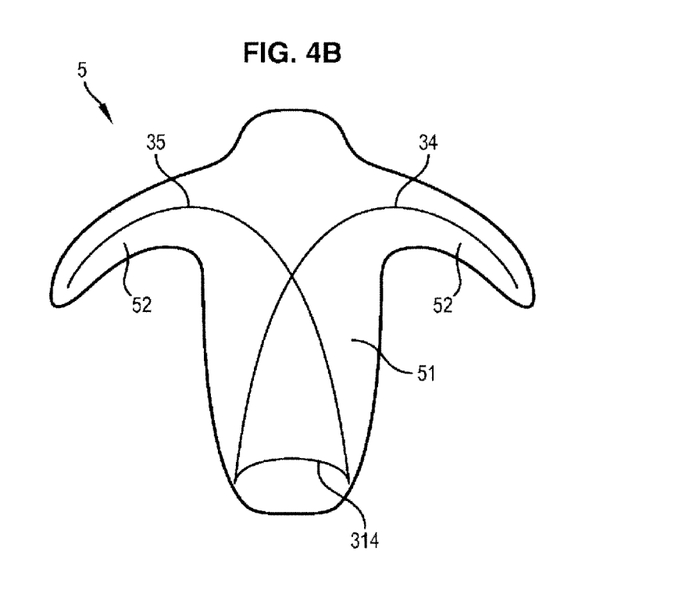

According to a second variant illustrated FIGS. 4A and 4B, the implant comprises an anterior part (FIG. 4A) that is rectangular shaped. The anterior part 4 has a short side having a length of between 8 centimeters and a long side having a length of around 12 centimeters. Bracings 36, 37, 311, 312 extend along the edges of the anterior part. The anterior part 4 is intended to be positioned at the neck of the bladder and the posterior part 5 is intended to the positioned at the fundus.

The implant 1 comprises a posterior part 5 (FIG. 4B) having a central portion 51 in the shape of a rectangle and two lateral portions 52 forming wings. The posterior part 5 comprises two arched bracings 34 and 35, each bracing extending from one end of a wing as far as a corner of the rectangle. The bracings are arranged in an X-configuration; they intersect at the central portion of the posterior part.

Figure 5A:
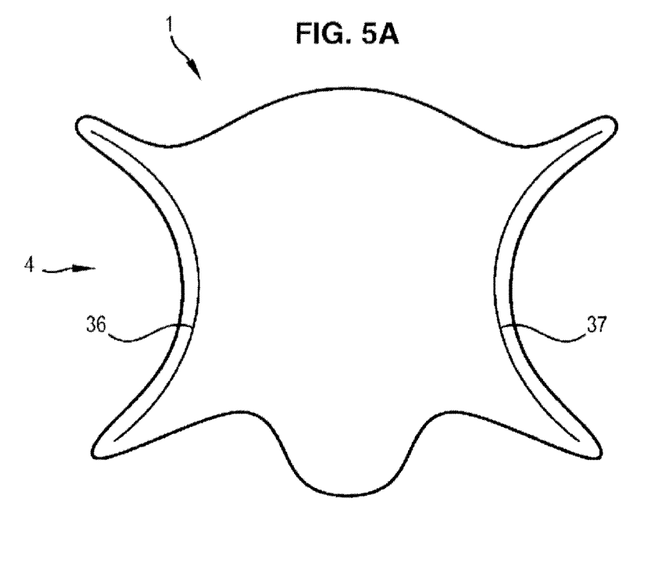
Figure 5B:
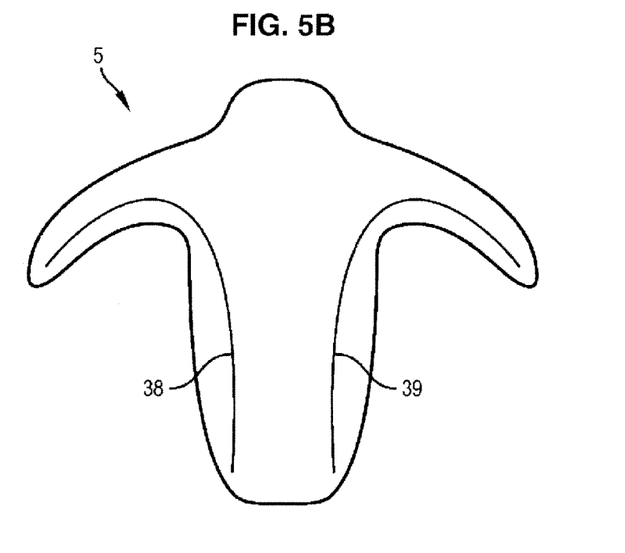

According to a third variant illustrated FIGS. 5A and 5B, the implant 1 comprises an anterior part 4 (FIG. 5A) of rectangular shape similar to the anterior part 4 of the implant in FIG. 4A. In this variant, two bracings 36, 37 extend along the side edges of the anterior part 4.

Similarly, the posterior part (FIG. 5B) is of similar shape to the posterior part of the implant in FIG. 4B. In this variant, two bracings 38, 39 extend along the side edges of the posterior part 5.

Figure 6A:
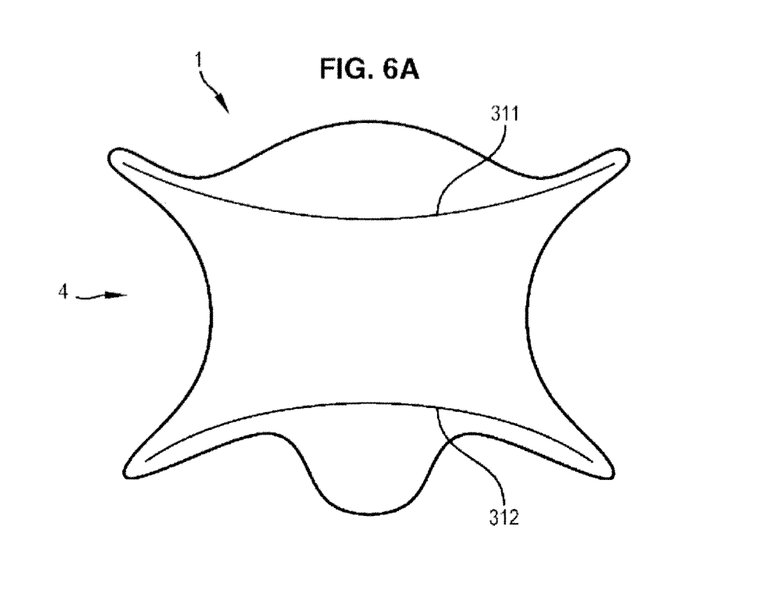
Figure 6B:
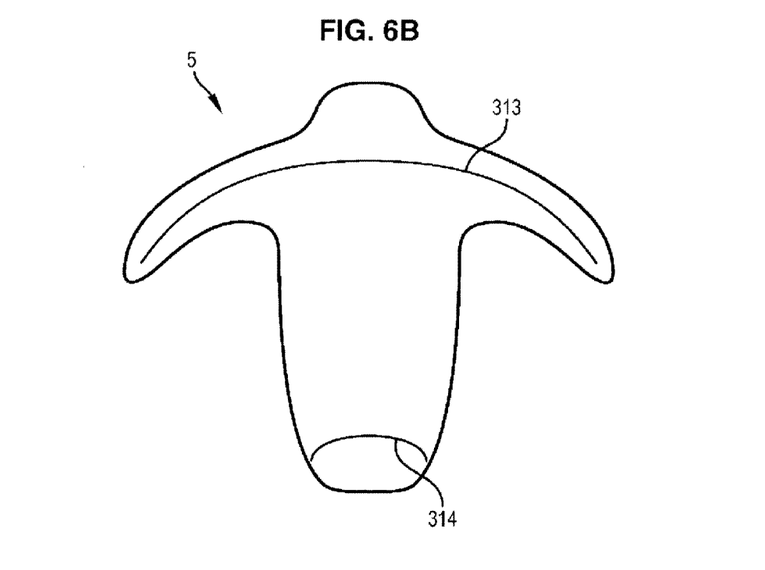

According to a fourth variant shown FIGS. 6A and 6B, the implant 1 comprises an anterior part 4 (FIG. 6A) of rectangular shape similar to the anterior part of the implant in FIG. 4A. In this variant, two bracings 311, 312 extend along the anterior and posterior edges of the anterior part 4 of the implant.

Similarly, the posterior part (FIG. 6B) is of similar shape to the posterior part 5 of the implant 1 in FIG. 4B. In this variant, the posterior part 5 comprises a first bracing 313 extending along an anterior edge of the posterior part between each of the ends of the wing-forming lateral portions, and a second bracing 314 extending along a posterior edge of the posterior part.

Figure 7A:
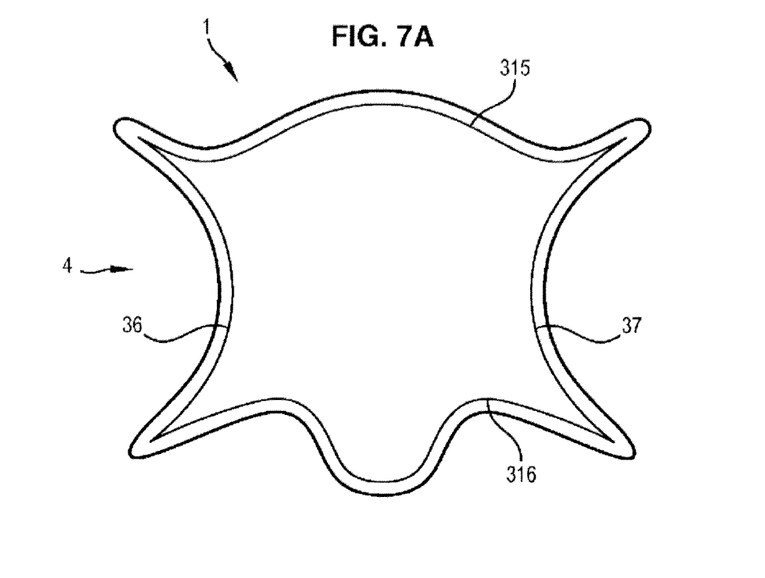
Figure 7B:
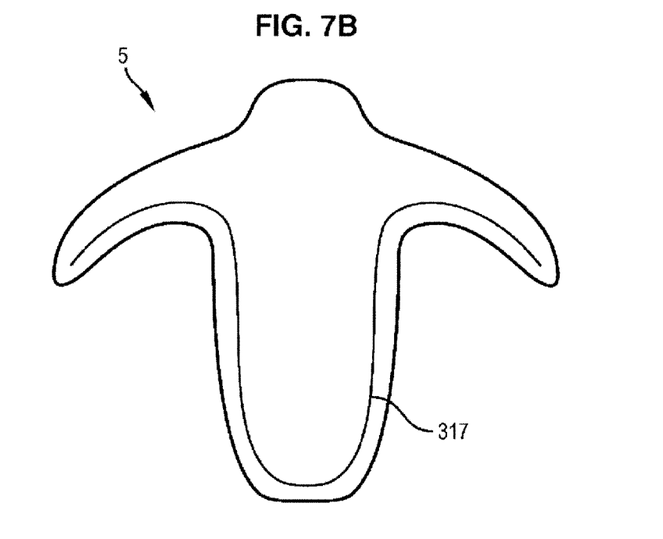

According to a fifth variant illustrated FIGS. 7A and 7B, the implant 1 comprises an anterior part 4 (FIG. 7) of rectangular shape similar to the anterior part of the implant in FIG. 4A. In this variant, fours bracings 36, 37, 315, 316 extend along the side edges of the anterior edge and of the posterior edge of the anterior part.

Similarly, the posterior part 5 (FIG. 7B) is of similar shape to the posterior part of the implant in FIG. 4B. In this variant, a single bracing 317 extends along the edges of the posterior part between each of the ends of the wing-forming lateral portions.

Figure 8A:
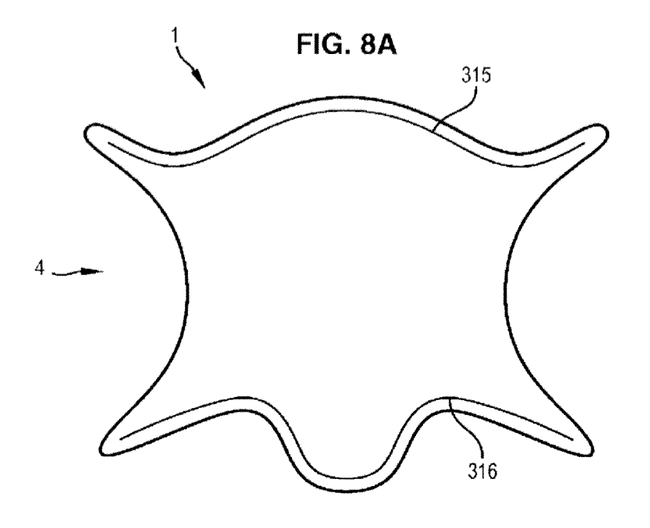
Figure 8B:
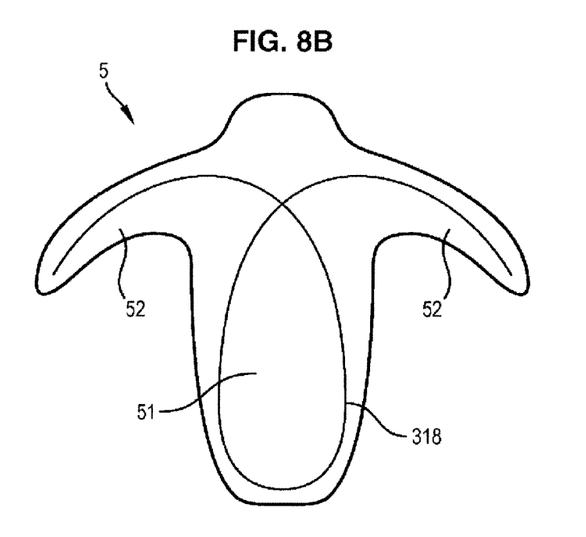

According to a sixth variant illustrated FIGS. 8A and 8B, the implant 1 comprises an anterior part 4 (FIG. 8A) of rectangular shape similar to the anterior part of the implant in FIG. 4A. In this variant, two bracings 315, 315 extend along the anterior edge and posterior edge respectively of the anterior part.

Similarly, the posterior part 5 (FIG. 8B) is of similar shape to the posterior part of the implant in FIG. 4B. In this variant, a single bracing 381 extends from one end of one of the lateral portions 52 as far as one end of the other lateral portion, forming a loop around the central portion 51.

Figure 9A:
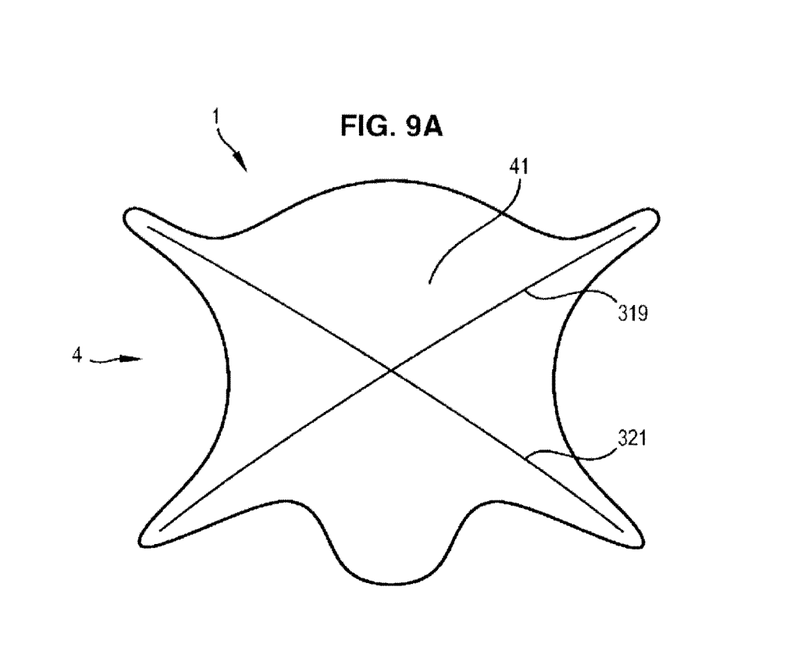
Figure 9B:
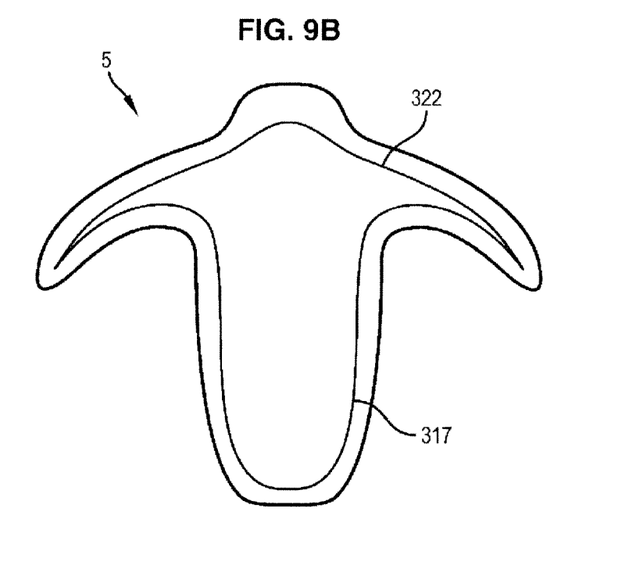

According to a seventh variant illustrated FIGS. 9A and 9B, the implant 1 comprises an anterior part 4 (FIG. 9A) having a rectangular shape similar to the anterior part of the implant in FIG. 4A. In this variant, two bracings 319, 321 extend along diagonals of the rectangle. The bracings 319, 321 are arranged in an X-configuration: they intersect at the central portion 41 of the anterior part.

Similarly, the posterior part 5 (FIG. 9B) is of similar shape to the posterior part of the implant in FIG. 4B. In this variant, two bracings 317, 322 each extend from one end of one of the lateral portions 52 as far as one end of the other lateral portion. One of the bracings 322 extends along an anterior edge of the posterior part whilst the other bracing 317 extends along the side edges and the posterior edge of the posterior part.

Positioning the Implant in the Pelvic Cavity in Relation to Different Forms of Prolapse.

The treatments for prolapse are performed as follows:

The patient is given general, local or loco-regional anaesthesia depending on the patient's condition. The position of the patient on the operating table is the position conventionally used by persons skilled in the art, namely the gynaecological position.

Before placing the prosthesis (or implant) in position a local infiltration of adrenalized xylocain in the region intended to receive the prosthesis is performed, followed by dissection of this region. Depending upon the type of prolapse to be treated, hysterectomy may be necessary before anterior or posterior dissection of the vagina.

For anterior dissection of the vagina, the anterior vaginal wall is held by means of 3 atraumatic clips while the surgeon makes a full thickness dissection of the anterior vaginal wall. Dissection is continued by vaginal incision as far as a point located at around 3 centimeters away from the urethral meatus to protect the region of the neck of the bladder. The bladder is dissected laterally as far as the fornix of the vagina. A finger can easily enter the paravesical fossa. The tendinous arch of the pelvic fascia on the posterior face of the pubic arch is identified over its entire length i.e. as far as the ischial spine. Procedure is performed on the right and left sides of the anterior vaginal walls.

Posterior dissection is conducted by performing a full vaginal thickness dissection of the posterior vaginal wall. Dissection starts from the vaginal incision and is continued as far as the vaginal apex. Laterally the dissection opens up the pararectal spaces and follows the space between the rectum and the levator ani muscle until it is possible to palpate the sacrospinous ligament. Dissection is performed on the posterior right and left side of the vagina.

The implant 1 allows the treatment of an anterior prolapse whilst preserving the uterus or removing the uterus via a hysterectomy, or a posterior prolapse with or without hysterectomy, or an anterior and posterior prolapse with or without hysterectomy. For an anterior or posterior prolapse, a partial prosthesis is used i.e. the anterior or posterior part of the implant. For prolapse that is both anterior and posterior a total prosthesis is used i.e. both the anterior and posterior parts of the implant.

Treating Anterior Prolapse with Hysterectomy

To treat anterior prolapse with hysterectomy, conventional vaginal hysterectomy is performed via a circular incision of the cervix preserving the utero-sacral ligaments. These ligaments are set aside while the surgeon carries out peritonization with continuous suturing using Vicryl 2/0. Once anterior dissection is completed, it is possible to place the anterior part of the prosthesis in position. The two proximal bearing portions of the prosthesis (referenced 421) are pressed between thumb and forefinger to hold the prosthesis in a folded configuration. The prosthesis is slid as far as the pubococcygeal insertion of the muscles using the finger or blunt instrument, optionally through the cut-out provided for this purpose. The sides of the two distal or deep bearing portions (referenced 422) are also pressed between thumb and forefinger to hold the prosthesis in folded configuration. The prosthesis is slid as far as the ischial spine, the distal bearing portions 422 positioning themselves just above the ischial spine with the help of the finger or blunt instrument, optionally in the cut-out provided for this purpose. By releasing the pressure exerted by the fingers or blunt instrument, the prosthesis opens out and positions itself tension-free below the bladder, whilst ensuring lateral contact against the tendinous arch of the pelvic fascia. The connecting part 6 (forming a posterior or deep end of the anterior prosthesis) is attached to the uterosacral ligaments using 2/0 prolene suture material. Closure of the vagina is performed with continuous Monocryl 2/0 suture. It may be necessary to adjust this positioning so that the anatomical elements lie perfectly in place.

Treating Anterior Prolapse with Preservation of the Uterus

For the treatment of anterior prolapse with preservation of the uterus, an anterior transverse colpotomy is performed allowing retrograde dissection or a longitudinal median incision as far as 3 centimeters away from the urethral meatus. The bladder is dissected laterally as far as the fornix of the vagina.

The finger is able easily to enter the paravesical fossa so that it is possible to identify the tendinous arch of the pelvic fascia over its entire length, from the posterior face of the pubic arch as far as the ischial spine. The right and left sides of the vagina are prepared in the same manner. A Prolene 2/0 suture is prepared for later use at the anterior uterine isthmus 2 centimeters above the cervix. The anterior part 4 of the prosthesis is then placed in position by pressing the proximal bearing portions 421 of the prosthesis between the thumb and forefinger so as to hold the anterior part 4 in folded configuration. The folded anterior part 4 is inserted at the anterior uterine isthmus 2 centimeters above the cervix.

The proximal bearing portions 421 (the proximal part faces the muscular insertions and the deep distal part faces the cervix which it helps to reposition anatomically) are pressed between the thumb and forefinger so as to hold the anterior part 4 in folded configuration. The proximal bearing portions 421 are inserted at the pubococcygeal insertion of the muscles using a finger or blunt instrument, optionally in a cut-out provided for this purpose. The distal or deep bearing portions 422 are also pressed between thumb and forefinger to hold the anterior part 4 in folded configuration. The distal bearing portions 422 are inserted as far as the ischial spine, the distal bearing portions 422 positioning themselves just above the spine by means of the finger or optionally a blunt instrument via a cut-out provided for this purpose. Once the anterior part 4 of the prosthesis is positioned at the desired point, the fingers or blunt instrument are removed allowing the opening of the prosthesis and its tension-free positioning below the bladder, whilst ensuring lateral contact against the tendinous arch of the pelvic fascia.

The connecting part 6 (forming a posterior or deep end of the anterior portion 4 of the prosthesis) is attached to the anterior face of the isthmus using the pre-prepared suture. Finally, the vagina is closed with continuous Monocryl 2/0 suturing.

Treatment of Posterior Prolapse with Hysterectomy

Posterior prolapse with hysterectomy is treated using a posterior portion 5. Conventional vaginal hysterectomy is performed via circular cervical incision. The utero-sacral ligaments are left aside. The peritoneum is closed with Vicryl 2/0 continuous suturing. A posterior vaginal incision is made with sagittal colpotomy of the lower half of the vagina as far as the vulva followed by posterior left and right dissection of the vagina (supra). The posterior portion 5 of the prosthesis can then be positioned in the dissection space by pressing the bearing portions 521 between thumb and forefinger to hold the prosthesis in folded configuration. The posterior portion 5 thus folded is slid into position either side using a finger or a blunt instrument, optionally via a cut-out provided for this purpose. The lateral bearing portions 52 are positioned bearing against the anterior face of the levator ani muscles. The fingers or blunt instrument are removed, releasing the pressure exerted on the bearing portions 521 and allowing deployment of the prosthesis in the dissection space. The connecting portion 6 forming an anterior part of the posterior portion is attached to the posterior face of the isthmus using the pre-prepared suture. The tail of the prosthesis left free on the perineum. The vaginal incision is then closed with Monocryl 0 continuous suture.

Treatment of Posterior Prolapse with Preservation of the Uterus

The posterior portion 5 of the prosthesis is used for treating posterior prolapse with preservation of the uterus using the following method. A posterior vaginal incision is made by sagittal colpotomy of the lower half of the vagina as far as the vulva. Right and left posterior dissection is performed as described above. A Prolene 2/0 suture is prepared for later use at the posterior uterine isthmus, 2 cm above the cervix (it will later be attached to the cervix if deemed useful or necessary by the surgeon). The posterior part 5 of the prosthesis is held folded and placed in the dissection space in the following manner. The bearing portions 521 are pressed between the thumb and forefinger to hold the posterior part 5 folded. The bearing portions 521 are inserted either side of the anus using a finger or blunt instrument, optionally in a cut-out provided for this purpose. The lateral bearing portions 52 are caused to bear against the anterior face of the levator ani muscles. The prosthesis is deployed spontaneously when the pressure exerted on the bearing portions 52 is released. The connecting portion 6 forming an anterior part of the posterior portion 5 is attached to the utero-sacral ligaments (using suture, glue, staples as decided by the surgeon and local conditions . . . ). The tail of the prosthesis is left free on the perineum. The vaginal incision is closed using Monocryl 0 continuous suturing.

Treatment of Anterior and Posterior Prolapse with Hysterectomy

Prolapse requiring removal of the uterus starts with a vaginal hysterectomy. Hysterectomy is performed following the conventional technique with circular incision around the cervix. The utero-sacral ligaments are preserved and left aside. Right and left anterior dissection of the vagina is initially made, followed by a posterior vaginal incision to carry out right and left posterior dissection of this organ. The incision entails supplementary sagittal colpotomy of the lower half of the vagina as far as the vulva.

The placing in position of the anterior part 4 of the prosthesis is carried out as follows. The proximal bearing portions 421 are pressed between the thumb and forefinger to hold the anterior part 4 folded. The proximal bearing portions 421 are inserted using a finger or blunt instrument, optionally via a cut-out provided for this purpose. The distal bearing portions 422 are also pressed between thumb and forefinger. The distal bearing portions 422 are inserted as far as the ischial spine, these distal bearing portions 422 being positioned just above the spine using a finger or blunt instrument, optionally via a cut-out provided for this purpose. The prosthesis is spontaneously deployed when the pressure exerted on the distal bearing portions 422 is released. However, the prosthesis is not yet in its final position.

The part 4 is positioned tension-free below the bladder, whilst ensuring lateral contact against the tendinous arch of the pelvic fascia.

The connecting portion 6 of the total prosthesis is positioned in the posterior dissection behind the vaginal apex. The utero-sacral ligaments are inserted between the prosthesis and the vagina.

The placing in position of the posterior part 5 of the prosthesis is made as follows. The bearing portions 521 are pressed between thumb and forefinger to hold the prosthesis in folded configuration. The bearing portions 521 are inserted either side of the anus as far as the sacrospinous ligament on which they are placed using a finger or blunt instrument optionally via a cut-out provided for this purpose. The lateral bearing portions 52 are caused to bear against the anterior face of the levator ani muscles. The tail of the prosthesis is left free on the perineum. The vaginal incisions are then closed with continuous suture using Monocryl 0.

Treatment of Anterior and Posterior Prolapse with Preservation of the Uterus.

An anterior and posterior prolapse can be also be treated by preserving the uterus and implanting a total prosthesis including two parts 4 and 5. The procedure is then as follows.

To treat the anterior prolapse, an anterior transverse colpotomy is performed thereby allowing retrograde dissection as far as 3 centimeters from the urethral meat. The bladder is dissected laterally as far as the fornix of the vagina. A finger can easily enter the paravesical fossa and allows the identification of the tendinous arch of the pelvic fascia over its entire length from the posterior face of the pubic arch as far as the ischial spine. These procedures are performed on the right and left side of the vagina. A Prolene 2/0 suture is pre-prepared at the anterior uterine isthmus, 2 centimeters above the cervix. The dissection space is ready to receive the folded anterior prosthesis. The proximal bearing portions 421 of the prosthesis are pressed between thumb and forefinger to hold the anterior part 4 of the prosthesis in folded configuration. The proximal bearing portions 421 are inserted using a finger or blunt instrument, optionally via a cut-out provided for this purpose. The distal or deep bearing portions 422 are also pressed between thumb and forefinger to hold the anterior part 4 of the prosthesis in folded configuration. The distal bearing portions 422 are inserted as far as the ischial spine using a finger or blunt instrument, optionally via a cut-out provided for this purpose. The distal bearing portions 422 are placed just above the spine providing for its anatomic support. After removing the blunt instrument or finger the anterior part 4 of the prosthesis is spontaneously deployed and positions itself tension-free below the bladder whilst ensuring lateral contact against the tendinous arch of the pelvic fascia. The connecting portion 6 forming a posterior or deep end 4 of the prosthesis is attached to the anterior face of the isthmus using the pre-prepared suture. The vagina is closed with continuous suturing using Monocryl 2/0 suture material.

The posterior prolapse is then treated as follows. A posterior vaginal incision is made by sagittal colpotomy of the lower half of the vagina as far as the vulva. Right and left posterior dissection is performed so as to create a space for placing the prosthesis in position. The proximal bearing portions 521 are pressed between the thumb and forefinger to hold the posterior part 5 in folded configuration. The proximal bearing portions 521 are inserted either side of the anus using a finger or blunt instrument, optionally via a cut-out provided for this purpose. The lateral bearing portions 52 are caused to bear against the anterior face of the levator ani muscles. The connecting portion 6 forming an anterior part of the posterior part 5 is attached to the utero-sacral ligaments. The tail of the prosthesis is left free on the perineum. Closing of the vaginal incision is then performed by continuous suture using Monocryl 0 suture material.

Complete prolapse can also be treated with a prosthesis formed of a single piece. This treatment is performed with removal of the uterus i.e. hysterectomy followed by transverse incision at the hysterectomy scar or at the apex of the prolapse. Right and left anterior dissection of the vagina is performed. A further posterior vaginal incision is made by supplementary sagittal colpotomy of the lower half of the vagina as far as the vulva so as to achieve right and left posterior dissection as previously described. The space is ready to receive the single-piece prosthesis in the following manner.

The proximal bearing portions 421 of the prosthesis are pressed between thumb and forefinger to hold the anterior part 4 of the prosthesis in folded configuration. The proximal bearing portions 4231 are inserted using a finger or blunt instrument, optionally via a cut-out provided for this purpose. The distal or deep bearing portions 422 are also pressed between thumb and forefinger to hold the anterior part 4 of the prosthesis in folded configuration. The distal bearing portions 422 are inserted as far as the ischial spine using a finger or blunt instrument, optionally via a cut-out provided for this purpose. The prosthesis is positioned tension-free below the bladder whilst ensuring lateral contact against the tendinous arch of the pelvic fascia.

The connecting portion 6 of the total prosthesis is positioned in the posterior dissection, behind the vaginal apex. The utero-sacral ligaments are inserted between the prosthesis and the vagina.

The proximal bearing portions 521 are pressed between the thumb and index to hold the posterior part 5 in folded configuration. The proximal bearing portions 521 are inserted either side of the anus using a finger or blunt instrument, optionally via a cut-out provided for this purpose. The lateral bearing portions 52 are caused to bear against the anterior face of the levator ani muscles. The tail of the prosthesis is left free on the perineum.

Continuous suturing with Monocryl 0 is used to close the vaginal incisions.

As will have been understood the implant just described has several advantages.

Since it does not require any specific attachment via suturing means, the implant can be placed in position following more simple procedure than used for existing techniques.

The positioning of the implant does not require the use of perforating guides or needles, which limits the risk of damage to adjacent vascular and nerve structures.

Additionally, since the implant does not have any suspension arms it is not necessary to form exit points in the skin, thus avoiding the onset of pain or infection at the emerging points.

Owing to its hollowed, three-dimensional shape, allowing it to mate the shape of the organ to be supported, the implant itself contributes to its own holding in position.

In particular the implant can be preformed (for example by moulding) with dimensions adapted to the specific anatomy of each patient.

Also, the bracing assembly limits the risk of retraction of the implant during the healing period.

And in the event of retraction of the implant, the risks of secondary reactions should be limited owing to the absence of points of attachment and suspension arms.

Finally, the absence of attachment points and suspension arms facilitates removal of the implant in the event of any further surgery.

The invention claimed is:

1. An implant for treating pelvic organ prolapse, comprising:
   a supporting portion comprising a first bracing defining a first frame and a first membrane portion disposed within said first frame, said first membrane portion being preformed to have a three dimensional shape, which three dimensional shape substantially fits around and is configured to mate to an organ to be supported, said organ having a generally rounded shape; and
   a bearing portion extending from the supporting portion and adapted to bear upon bone or ligament structures to stabilize the implant, the bearing portion comprising a second bracing defining a second frame substantially surrounding and extending from said first frame and a second membrane portion, said second membrane portion being held taut at said bearing portion by said second bracing.

2. The implant according to claim 1, wherein the supporting portion has a contour of general oval or elliptical shape.

3. The implant according to claim 1 or claim 2, wherein the membrane portions comprise a web comprised of interlaced fibres.

4. The implant according to claim 1 or claim 2, wherein said bearing portions are planar.

5. The implant according to claim 1 or claim 2, wherein the membrane portions comprise polypropylene, polyester or a material of animal or human origin.

6. The implant according to claim 1 or claim 2, comprising a bracing assembly formed by the bracing portions, the bracing assembly being able to be folded to allow insertion of the implant in the tissues, and to be deployed when the implant lies in working position.

7. The implant according to claim 6, wherein the bracing assembly is able to deploy spontaneously.

8. The implant according to claim 1 or claim 2, wherein the bracing assembly is formed of an absorbable material.

9. The implant according to claim 1 or claim 2, wherein the membrane portion of the supporting portion is hollow-preformed to support the bladder, and comprising a second supporting portion comprising a second membrane portion which is hollow-preformed to support the rectum.

10. The implant according to claim 9, comprising a connecting part between the first supporting portion and the second supporting portion.

11. The implant according to claim 10, wherein the connecting part comprises a zone of lesser resistance which can be broken to separate the first supporting portion from the second supporting portion.

12. A method for treating pelvic organ prolapse comprising a step of:
    making an incision in a wall of the vagina to form a space between the vagina and an organ to be supported,
    arranging in the space an implant according to claim 1 or claim 2 in a position in which the hollow-preformed membrane portion mates the shape of the organ to be supported, and the bearing portion(s) come to bear upon bone or ligament structures to stabilize the implant.

* * * * *